United States Patent
Berneth et al.

(10) Patent No.: US 6,936,325 B2
(45) Date of Patent: Aug. 30, 2005

(54) OPTICAL RECORDING MEDIUM

(75) Inventors: Horst Berneth, Leverkusen (DE); Friedrich-Karl Bruder, Krefeld (DE); Wilfried Haese, Odenthal (DE); Rainer Hagen, Leverkusen (DE); Karin Hassenrück, Düsseldorf (DE); Serguei Kostromine, Swisttal (DE); Peter Landenberger, Köln (DE); Rafael Oser, Krefeld (DE); Thomas Sommermann, Bergisch Gladbach (DE); Josef-Walter Stawitz, Odenthal (DE); Thomas Bieringer, Odenthal (DE); Yuichi Sabi, Tokyo (JP); Takashi Iwamura, Kamakura (JP); Mitsuaki Oyamada, Yokohama (JP); Hidetoshi Watanabe, Chiba (JP); Sakuya Tamada, Kodaira (JP); Masanobu Yamamoto, Yokohama (JP)

(73) Assignees: Sony Corporation, Tokyo (JP); Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/102,168

(22) Filed: Mar. 20, 2002

(65) Prior Publication Data
US 2003/0099807 A1 May 29, 2003

(30) Foreign Application Priority Data

| Mar. 28, 2001 | (DE) | 101 15 227 |
| Apr. 6, 2001 | (DE) | 101 17 462 |
| Apr. 6, 2001 | (DE) | 101 17 463 |
| Apr. 6, 2001 | (DE) | 101 17 464 |
| Apr. 6, 2001 | (DE) | 101 17 461 |
| May 21, 2001 | (DE) | 101 24 585 |
| Jul. 25, 2001 | (DE) | 101 36 064 |
| Jul. 25, 2001 | (DE) | 101 36 063 |
| Aug. 22, 2001 | (DE) | 101 40 165 |
| Oct. 4, 2001 | (EP) | 01123810 |
| Dec. 21, 2001 | (EP) | 01130527 |
| Jan. 9, 2002 | (DE) | 102 00 484 |
| Jan. 24, 2002 | (DE) | 102 02 571 |
| Feb. 20, 2002 | (EP) | 02003812 |
| Mar. 11, 2002 | (EP) | 02005505 |

(51) Int. Cl.$^7$ ................................. B32B 3/02
(52) U.S. Cl. ............ 428/64.8; 428/64.4; 428/64.2; 428/64.6
(58) Field of Search .............. 428/64.4, 64.6, 428/64.8, 64.2

(56) References Cited

U.S. PATENT DOCUMENTS

| 5,137,798 A | * | 8/1992 | Duggan et al. | 430/270.16 |
| 5,449,587 A | | 9/1995 | Itoh et al. | 430/273 |
| 5,502,172 A | * | 3/1996 | Pape et al. | 534/591 |
| 5,536,548 A | | 7/1996 | Koji et al. | 428/64.1 |
| 5,855,979 A | | 1/1999 | Umchara et al. | 428/64.1 |
| 6,345,034 B1 | | 2/2002 | Kim | 369/275.5 |
| 2002/0001691 A1 | * | 1/2002 | Sabi et al. | 428/64.4 |
| 2002/0009038 A1 | | 1/2002 | Kim | 369/112.23 |
| 2002/0076648 A1 | * | 6/2002 | Berneth et al. | 430/270.17 |

FOREIGN PATENT DOCUMENTS

| EP | 0 849 727 A2 | 6/1998 |
| EP | 0 971 344 A1 | 1/2000 |
| EP | 1 143 431 A2 | 10/2001 |

* cited by examiner

Primary Examiner—Deborah Jones
Assistant Examiner—G. Blackwell-Rudasill
(74) Attorney, Agent, or Firm—Diderico van Eyl

(57) ABSTRACT

An optical recording medium having at least a recording layer 11 and a light transmitting layer 13 formed on a substrate 10, in which the recording layer 11 is made of an organic material for absorbing an incident light of wavelength of 360 nm to 460 nm, and inducing physical change or chemical change to vary the refractive index, the light transmitting layer 13 is 10 μm to 177 μm in thickness, the relation between absorption coefficient "k" and pyrolysis temperature $T_{dec}$ of organic material is $$950(° C.) < (T_{dec} (° C.) - 20)/k < 4100° C. \quad (1),$$

and the absorption coefficient "k" is k>0.0.

3 Claims, 3 Drawing Sheets

24 LIGHT TRANSMITTING LAYER
23 SECOND Ag LAYER
22 RECORDING LAYER
21 FIRST Ag LAYER
10 SUBSTRATE

Fig. 3 (figure with 'Region A')
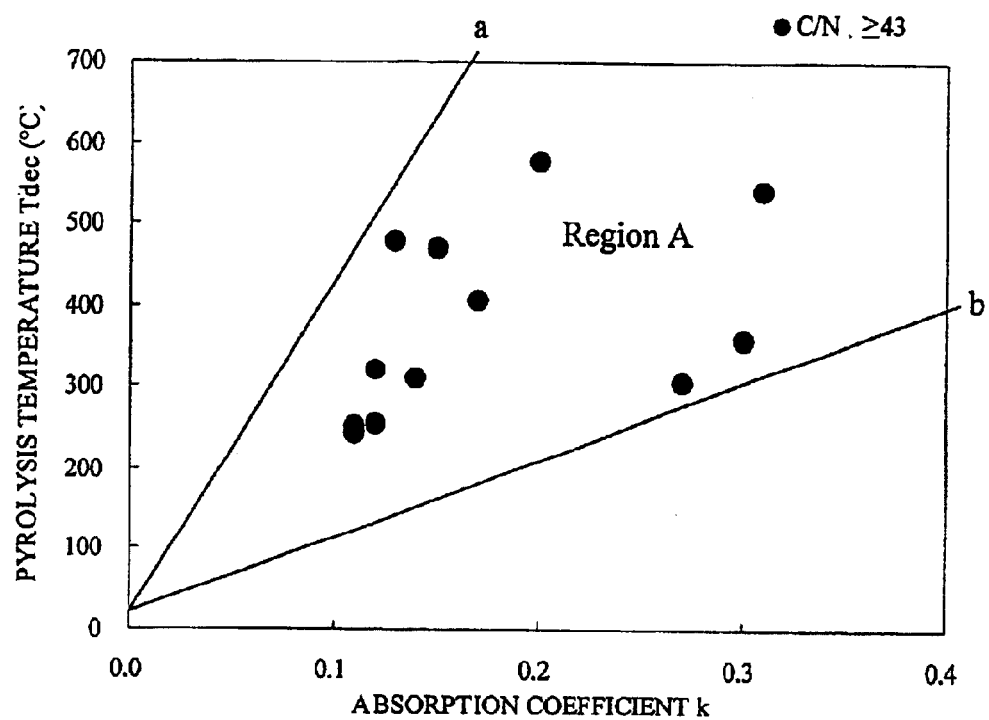

OPTICAL RECORDING MEDIUM

The present invention relates to an optical recording medium having a recording layer made of an organic material, such as CD-R (Compact Disc-Recordable) and DVD-R (Digital Video Versatile Recordable) and a process for its preparation.

PRIOR ART

Various optical recording media are produced, such as optical discs having recording layers made of various materials formed on substrates, for recording and reproducing information in the recording layers by irradiating light. In these optical recording media, a higher recording density is realized by methods of using light source of shorter wavelength and raising the numerical aperture of the objective lens.

Among these optical recording media, recording layers of CD-R and DVD-R are made of so-called organic pigment materials of organic matters which absorb incident light and are decomposed by physical change or chemical change, and vary the refractive index. Such optical recording media are compatible with other recording media, and are easy to manufacture and inexpensive, so that the sales are increasing year after year. In next-generation optical recording media, so-called write-once media using such organic pigment materials in the recording layer are being desired.

PROBLEMS THAT THIS INVENTION IS TO SOLVE

As the recording density becomes higher and the focused light spot diameter becomes smaller, optimization of organic pigment material is required. However, pyrolytic reaction mechanism of organic pigment on the optical recording medium is not fully clarified, and the CD-R and DVD-R have been actually optimized empirically by repeating experiments, and optimum characteristic values as next-generation high recording density media are not discovered yet, and at present there is no specific guideline for development of next-generation optical recording media using organic pigment material of this type in the recording layer.

In particular, organic pigments are available in a vast variety, and the thermal conductivity of organic pigment materials is extremely low as compared with phase change materials or magneto-optical materials, and only little data has been disclosed, and therefore accurate findings are hardly obtained about temperature rise during recording.

As the optical system corresponding to the next-generation optical recording media, the blue laser diode (LD) is put in practical use, and the light source is shortened in wavelength, and on the other hand, the objective lens with the numerical aperture (NA) of more than about 0.80 has been developed, and the light spot diameter is extremely smaller as compared with the conventional optical recording media. That is, the light energy is extremely higher as compared with the prior art, and optimization of thermal characteristics is the most difficult problem.

Moreover, since the wavelength of the recording and reproducing light source is different from the conventional wavelength, optimization of optical characteristics is needed in the aspect of materials, and the molecular structure of the organic pigment material must be designed newly. That is, the recording layer material must have an appropriate refractive index about the reproducing light source so as to allow a sufficiently large amplitude of reproduced signals.

At the same time, it is also necessary to optimize the absorption coefficient at this wavelength. The absorption coefficient is related to temperature rise in recording, and the optimum value varies with the focused light spot diameter, and hence optimization of absorption coefficient substantially determines the recording characteristics.

Thus, the wavelength of light source is different and the numerical aperture of objective lens is different, too, and it is practically impossible to use the conventional organic pigment material as it is, and in particular in the case of combination of blue LD light source and high NA, a completely different material from the conventional materials is demanded.

In the optical system of the recording and reproducing apparatus of next-generation optical recording medium, as mentioned above, the blue LD light source and the objective lens of numerical aperture of about NA=0.8 or more are used. What is particularly different in this case from the conventional optical recording medium is the thickness of the light transmitting layer.

In the conventional CD and DVD, recording layer and others are formed on a light permeable substrate of about 1.2 mm and 0.6 mm, respectively, and the substrate side is the light incident side. On the other hand, in the next-generation optical recording medium applicable to the lens advanced in NA, about 0.80 to 0.95, it is required to assure a practical skew margin, that is, to assure a tolerance about skew of the substrate side of the medium to the optical system of the optical pickup, and coma aberration takes place when skew is generated. So, in order to solve the problem of increase of coma aberration, there is a tendency of selecting the thickness of light transmitting layer in a range of 10 $\mu$m to 177 $\mu$m.

At present, fabrication of such light transmitting layer itself is a subject of development, but, in other words, the medium reduced in thickness of light transmitting layer aims at high density recording in the aspect of application of optical system of high NA.

In the light of such circumstance, it is hence an object of the invention to select an organic material having adequate optical constant and thermal characteristics as the recording layer, and present an optical recording medium for realizing favorable recording and reproducing characteristics by recording at high density by using such material.

The invention presents an optical recording medium having at least a recording layer and a light transmitting layer formed on a substrate, in which the recording layer is made of an organic material for absorbing an incident light of wavelength of 360 nm to 460 nm, and inducing physical change or chemical change to vary the refractive index, the light transmitting layer is 10 $\mu$m to 177 $\mu$m in thickness, the relation between absorption coefficient (k) and pyrolysis temperature Tdec of the organic material is 950 (° C.)<(Tdec (° C.)−20)/k<4100° C. . . . (1), and the absorption coefficient "k" is k>0.0.

Therefore $T_{dec}$ is greater than 20° C., preferably greater than 50° C. and most preferably greater than 100° C.

As mentioned above, in the invention, by selecting the organic material of the recording layer to satisfy the relation between absorption coefficient (k) and pyrolysis temperature Tdec as defined in formula (1) and to have the absorption coefficient of over 0.0, the recording and reproducing characteristics by the blue light source of short wavelength and optical pickup of high numerical aperture NA are improved, so that a practical optical recording medium capable of recording at high density can be realized.

Referring now to the drawings, preferred embodiments of the invention are described in detail below, but it must be noted that the invention is not limited to each embodiment below, but may be changed and modified within a range not departing from the true spirit and scope of the invention.

Thus, the invention is intended to give an optimum range of absorption coefficient and pyrolysis temperature of recording layer material in optimizing the thermal characteristics of the recording layer. The optimum composition suited to optical recording medium using the optical system for next-generation optical recording medium as mentioned above, and preferably aims at recording and reproducing in an optical system with the numerical aperture NA of the objective lens of the optical pickup of 0.80 or more, by employing a so-called blue light source of wavelength of 360 nm to 460 nm and selecting the thickness of the light transmitting layer in a range of 10 μm to 177 μm.

When the recording layer is made of an organic material for recording by so-called pyrolysis of physical change or chemical change by absorbing incident light, the recording characteristics and reproduction stability are determined to some extent by the relation between the absorption coefficient and pyrolysis temperature. In particular, the amount of heat that the recording layer absorbs from a constant amount of light energy is primarily proportional to the absorption coefficient. This mechanism is explained below.

The temperature distribution in the recording layer can be calculated by using a thermal conductivity formula (for example, O. W. Shih, J. Appl. Phys. 75 (1994) 4382). The solution of the thermal conductivity formula depends on various parameters such as film composition, thermal conductivity of each layer, recording light pulse pattern, linear velocity, and spot size of incident light.

In the parameters of an optical recording medium, when an organic pigment is used in the recording layer, since the thermal conductivity of the recording layer is extremely low, the speed of heat conduction to the surrounding is slow, and for example, it is about 1/500 of aluminium thin film, or about 1/5 of glass substrate. Therefore, the maximum reaching temperature, that is, the temperature of the hottest area in the spot is largest in the dependence on the heat absorption to the recording layer, that is, the absorption heat amount $(-\nabla \cdot <S>)$ calculated from the pointing vector $<S>$.

As for the pointing vector, since the recording layer is a thin film, effects of multiple interference must be taken into consideration, but the higher the absorption coefficient "k", the higher becomes the absorption heat amount, and primarily it may be assumed to be proportional to the absorption coefficient "k". That is, the temperature before recording is room temperature, being about 20° C., but as the absorption coefficient becomes higher, the maximum reaching temperature tends to elevate almost linearly.

In recording of organic material, pyrolysis is the principle of recording. As a result of reaction and dissociation of molecules by pyrolysis, the optical constant after recording changes, and it is detected by the reproducing light. Therefore, recording is performed as the recording layer partially reaches the pyrolysis starting temperature in the spot. The higher the pyrolysis temperature Tdec, the larger amount of heat is needed in recording, but in the existing optical recording apparatus in which the indent light intensity is limited in a certain range, a desired reaching temperature is obtained by properly selecting the absorption coefficient as mentioned above.

As organic material dyes and/or pigments are preferred. Such dyes and pigments especially belong to the following classes: azo, especially heterocyclic azo, merocyanines, hemicyanines, cyanines, strepto cyanines, zero cyanines, enamine, hydrazone coumarines and phthalocyanines. These dyes or pigments can also be polymeric or bound to a polymeric backbone. Most preferred are the classes of dyes and pigments to which the embodiments 1 to 12 belong to.

Taking note of such relation between absorption coefficient and pyrolysis temperature, recordable examples and non-recordable examples are shown below, and a favorable range of absorption coefficient and pyrolysis temperature is presented.

In the following embodiments, the pyrolysis temperature Tdec was measured by a Differential Scanning Calorimeter (DSC) and calculated from the so-called DSC curve. To separate from the peak of dissolution temperature in the DSC curve, Thermogravimetric Analysis (TGA) was also conducted, and a peak without change in mass was judged to be dissolution, and a peak of DSC curve in a region lowered by 5% or more in mass in the TGA was judged to be pyrolysis temperature $T_{dec}$.

In each example, the recording and reproducing characteristics were evaluated by using an optical device comprising a blue light source of wavelength of 405 nm and an objective lens of optical pickup with numerical aperture NA of 0.85. In a preferred embodiment of the present invention the reflectivity of the optical recording medium is greater than 10%.

In the optical recording medium, the very preferable C/N level is not specific but is about 45 dB. In recording materials in process of development, considering there is fluctuation of 2 to 3 dB of C/N only by optimizing of film forming condition and recording condition, in the invention, materials capable of obtaining C/N of preferably 43 dB or more are assumed to be well recordable organic materials at present. That is, when the C/N is 43 dB or more, it is estimated to satisfy the preferred requirements for optimizing as the design of recording layer best.

The method of measuring the C/N value of this application is using a spectrum analyzer having a resolution band with 30 kHz.

Incidentally, if the thermal characteristics of the recording layer are not suited to the optical system employed in the recording apparatus, the C/N is lowered significantly, and therefore by checking if the preferred C/N of about 43 dB is obtained or not, the characteristics of the material may be approximately clarified.

First Embodiment

In this example, as shown in a schematic magnified sectional view in FIG. 1, a recording layer 11, a dielectric layer 12, and a light transmitting layer 13 were sequentially laminated on a substrate 10, and an optical recording medium was formed. The substrate 10 is a polycarbonate substrate, and, although not shown, guide grooves are formed in the substrate at track pitches of 0.64 μm, and the width of guide grooves is about 50% of the track pitch so that data can be recorded in both grooves and lands between grooves. That is, the substantial track pitch is about 0.32 μm. The depth of grooves is 40 nm.

The material of recording layer 11 is triphenyl amine tetramer. More specifically, it is N,N'-Bis(4-diphenylamino-4-biphenyl)-N,N'-diphenylbenzidine, and CasNo. is 167218-46-4. The film forming method is the vapor deposition process, and the film thickness is 40 nm. As the optical constant, the refractive index "n" to the light source of 405 nm before recording is 2.31, the absorption coefficient "k" is 0.13, the pyrolysis temperature $T_{dec}$ is 480° C.

The dielectric layer 12 is $SiO_2$, which is formed in a film thickness of 40 nm by sputtering method. The purpose of the dielectric layer 12 is to protect the recording layer 11.

The thickness of the light transmitting layer is 100 μm. This layer is formed by gluing polycarbonate sheets by using pressure sensitive adhesive (PSA), and the combined thickness is set at 100 μm.

In thus fabricated optical recording medium, the refractive index "n" of the substrate is about 1.6, and the refractive index "n" of the pressure sensitive adhesive is about 1.5, and therefore reflection occurred at the interface of upper and lower side of the recording layer 11 to induce multiple reflections, and the reflectivity to light of wavelength of 405 nm became about 15%. The optical recording medium composed of materials in which refractive index of recording layer is higher than the refractive index of substrate is hereinafter called L type.

In recording, the linear velocity was 5.72 m/s, the reproducing light power was 0.3 mW, and the recording pattern was a single carrier with mark length of 0.69 μm. For recording a single mark, seven pulse trains of the same width were entered at pulse/space ratio 50%, the peak power was 5.0 mW, and the C/N (carrier/noise ratio) was measured by a spectrum analyzer, and the recording and reproducing characteristics were evaluated. The spectrum analyzer was TR4171 of Takeda Riken, and the RBW was set at 30 kHz.

As a result of the above-described measurement, a value of 54.0 dB was obtained in the optical recording medium of this embodiment. This organic material is known to bring about sufficiently excellent recording and reproducing characteristics.

Second Embodiment

In this example, the organic material of formula (I) was used as the material for the recording layer. The absorption coefficient (k) of this material is 0.12, and the pyrolysis temperature Tdec is 322° C. The refractive index (n) is 1.30, and since the reflectivity is too low in this material alone, as shown in a schematic magnified sectional view in FIG. 2, a first Ag layer 21, a recording layer 22, a second Ag layer 23, and a light transmitting layer 24 were sequentially laminated on a substrate 10.

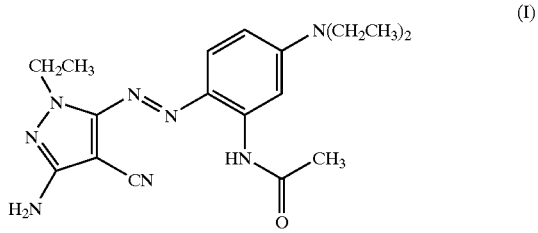

(I)

Herein, the material, thickness, configuration, and film forming method of the substrate 10 and light transmitting layer 24 are the same as in a first embodiment. The thickness of the first Ag layer 21 is 12 nm, the thickness of the second Ag layer is 10 nm, and the thickness of the recording layer is 50 nm. The first and second Ag layers 21 and 23 were formed by DC sputtering method. The recording layer 21 was formed by spin coating method. In this configuration, the reflectivity was 20%.

In this example, the C/N was measured in the same recording and reproducing conditions as in the embodiment 1, and 45.5 dB was obtained.

Thus, since the recording layer 22 contacts with metal layers (Ag layers), problems due to difference in thermal characteristics were afraid of, but actually since the thickness of the Ag layers 21 and 23 is extremely small, 10 to 12 nm, the thermal conductivity is not practically different from that of the dielectric layer in the first embodiment, and moreover since the thermal conductivity of the recording layer itself is extremely low, the temperature rise in the central part of the recording layer is almost the same as in the first embodiment.

In this configuration, since the incident light passes through the second Ag layer 23 and reaches the recording layer 22, the quantity of light is lowered, whereas the recording layer 22 has a structure of resonator enclosed by the first and second Ag layers 21 and 23, and induces multiple reflections, so that the heat absorption amount in the recording layer 22 is not very different from that in the first embodiment. Therefore, if the film composition is different from that in the first embodiment, in the same recording condition, the reaching temperature during recording seems to be nearly the same. Actually, by the triphenyl amine tetramer used as recording layer material in the first embodiment, when the recording layer is sandwiched between the Ag layers explained in FIG. 2, nearly the same recording sensitivity was obtained, and a similar C/N was measured.

The refractive index of the material before recording in the second embodiment was 1.3, and the refractive index approaches 1.5 after pyrolysis, and a signal was detected. Such material whose refractive index before recording is lower than that after recording is hereinafter called S-type.

As in the above-described first and second embodiments, in each material, the film compositions were classified into L type and S type depending on the refractive index, optical recording media were prepared in proper compositions, and recording and reproducing characteristics were measured in the same conditions as in the first embodiment.

More specifically explaining these film compositions, in the L type, basically, the film composition in the first embodiment was used. As for the S type material, basically, the film composition in the second embodiment was used, and when the initial refractive index was 1.2 or less, in order to simplify, the structure of the first embodiment, that is, using SiN as the material of the dielectric layer and the film was formed in a thickness of 40 nm. A sufficient reflectivity of about 15% was obtained.

Measured results of absorption coefficient "k", pyrolysis temperature and C/N of these materials are shown in Table 1 together with the results of the first and second embodiments.

TABLE 1

| embodiment | Formula of organic material | Type | Layer Structure same as in embodiment | Absorption Coefficient k | Pyrolysis temperature $T_{dec}$ (° C.) | C/N (dB) |
|---|---|---|---|---|---|---|
| 1 | (structure: tetrakis(diphenylamino)-substituted biphenyl derivative) | L | 1 | 0.13 | 480 | 54.0 |
| 2 | (pyrazole azo dye structure with $C_2H_5$, $N(C_2H_5)_2$, $H_2N$, CN, NHCOCH$_3$ groups) | S | 2 | 0.12 | 322 | 45.5 |
| 3 | (thiadiazole azo dye with diisopropylamino, OCH$_3$, N(CH$_2$CH$_2$OH)$_2$, NHCOCH$_3$ groups) | S | 2 | 0.11 | 244 | 45.6 |
| 4 | (thiadiazole azo dye with diisopropylamino, N(C$_2$H$_5$)$_2$, NHCOCH$_3$ groups) | S | 2 | 0.12 | 256 | 49.4 |
| 5 | (thiadiazole azo dye with diisopropylamino, N(C$_2$H$_5$)$_2$, NHSO$_2$CH$_3$ groups) | S | 2 | 0.11 | 252 | 44.8 |

TABLE 1-continued

| embodiment | Formula of organic material | Layer Structure same as in embodiment Type | Absorption Co-efficient k | Pyrolysis temperature $T_{dec}$ (° C.) | C/N (dB) |
|---|---|---|---|---|---|
| 6 | | L | 1 | 0.17 | 408 | 47.0 |
| 7 | | S | 1 | 0.30 | 358 | 57.0 |
| 8 | | L | 1 | 0.27 | 305 | 52.0 |
| 9 | | L | 1 | 0.14 | 312 | 48.0 |
| 10 | | L | 1 | 0.20 | 577 | 48.6 |

TABLE 1-continued

| embodiment | Formula of organic material | Type | Layer Structure same as in embodiment | Absorption Coefficient k | Pyrolysis temperature $T_{dec}$ (° C.) | C/N (dB) |
|---|---|---|---|---|---|---|
| 11 | | L | 1 | 0.31 | 544 | 55.0 |
| 12 | | L | 1 | 0.15 | 470 | 45 |

In FIG. 3, the bullet mark shows the preferred value of C/N of 43 dB or more relating to the absorption coefficient and pyrolysis temperature in the first to twelfth embodiments. Although the very preferred value is 45 dB as the practical signal level of optical recording medium, as mentioned above, a fluctuation of 2 to 3 dB is taken into consideration because it is likely to occur depending on the film forming condition and recording condition, and therefore favorable results are expected by improvement of film forming conditions when the C/N value is at least 43 dB or more, and hence 43 dB is selected as the preferred minimum value.

The system and molecular structure of the organic materials measured herein are varied and diversified (see Table 1) and as clear from FIG. 3, it is known that a clear tendency of recording and reproducing characteristics is expressed only by the physical parameters of absorption coefficient "k" and pyrolysis temperature Tdec. That is, it is known that area region A of bullet mark is excellent in recording and re-producing characteristics.

The maximum reaching temperature is primarily proportional to the absorption coefficient "k" as mentioned above. The ambient temperature in recording is room temperature, and by selecting the boundary by a straight line starting from the room temperature, the region of the absorption coefficient "k" and pyrolysis temperature Tdec which is excellent in recording and reproducing characteristics can be clarified. These lines are indicated as "a" and "b" in FIG. 3.

The range of region C enclosed by these lines "a" and "b" can be expressed as $950$ (° C.)$<$(Tdec (° C.)$-20$)/k$<4100$° C.

The absorption coefficient "k" is, of course, a value exceeding 0. This is because the recording layer material is properly selected so as to change in the refractive index by absorbing light and inducing physical change or chemical change.

When the substrate material is polycarbonate, it may melt when the temperature exceeds 1000° C., so that the pyrolysis temperature $T_{dec}$ is desired to be 1000° C. or below.

Materials shown in FIG. 3 are obtained as a result of careful selection so as to be sufficiently low in noise level before recording and maintain a high quality of evaluation so that the thermal characteristics can be evaluated. Conversely, as far as the organic materials have the relation of absorption coefficient and pyrolysis temperature within the range according to the invention, a favorable C/N can be obtained when the noise level before recording is low and basic characteristics are satisfied.

An example of high noise level is a case of formation of large grain boundary due to crystallization of the recording layer, or formation of diffusion or crack in the dielectric layer due to high flowability. Except for such special cases, as far as the recording layer is formed adequately, as the noise level, the combination of so-called disk noise due to pits and lands of substrate, shot noise originating from the light source such as laser, and thermal noise of detector is dominant, and the dependency on the material of recording layer is low.

Thus, the invention presents a recording material for practical optical recording medium of high recording density preferable applicable to an apparatus using an optical system having a so-called blue light source with wavelength of 360 nm to 460 nm, and an objective lens with numerical aperture NA of 0.80 or more.

The invention is not limited to the material composition in the embodiments herein.

Figure 1:
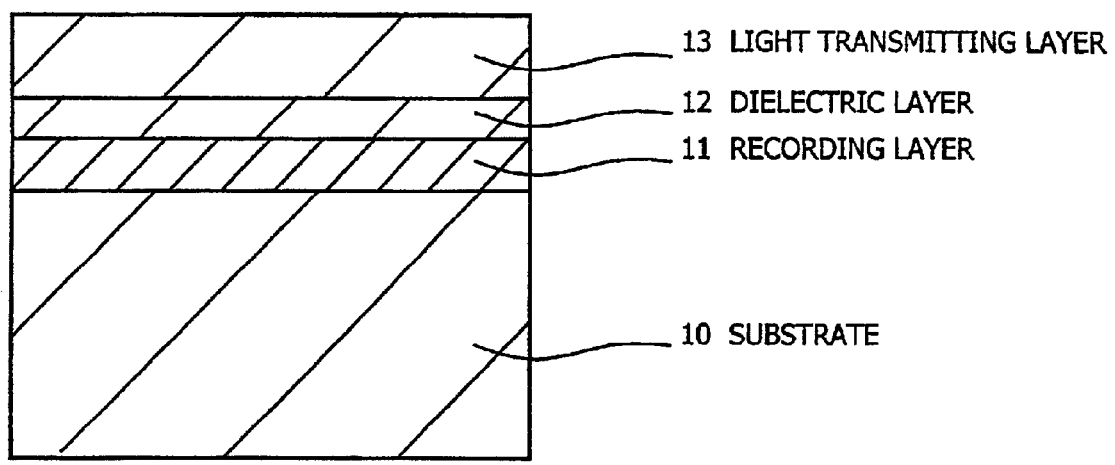
FIG. 1
Figure 2:
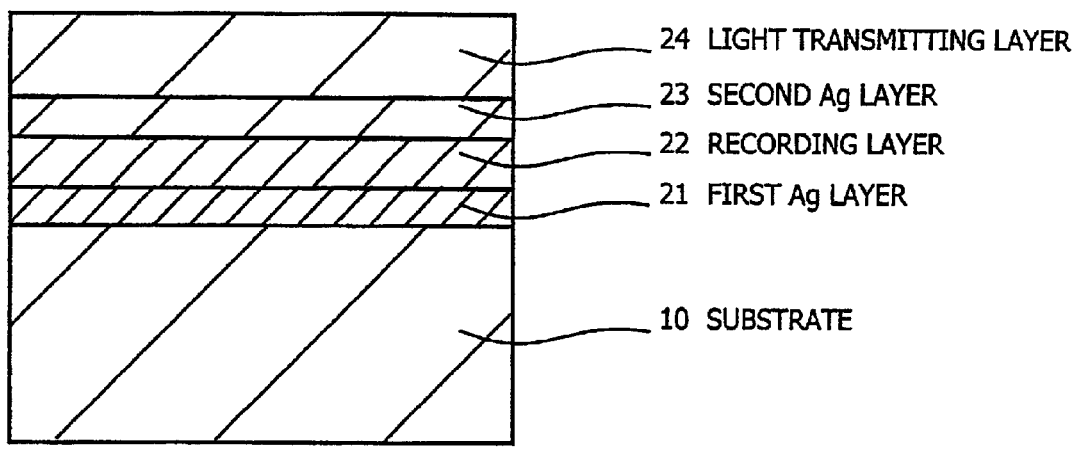

This is a schematic magnified sectional view of an example of optical recording medium.

FIG. 2

This is a schematic magnified sectional view of an example of optical recording medium.

FIG. 3

This is a diagram showing results of evaluation of recording and reproducing characteristics relating to absorption coefficient and pyrolysis temperature in each example of optical recording medium.

DESCRIPTION OF REFERENCE NUMERALS

10: Substrate
11: Recording medium
12: Dielectric layer
13: Light transmitting layer
21: First Ag layer
22: Recording layer
23: Second Ag layer
24: Light transmitting layer

What is claimed is:

1. An optical recording medium having at least a recording layer and a light transmitting layer formed on a substrate, characterized in that the recording layer is made of an organic material for absorbing an incident light of wavelength of from 360 nm to 460 nm, and inducing physical change or chemical change to vary its refractive index, the light transmitting layer is 10 μm to 177 μm in thickness, the relation between absorption coefficient (k) and pyrolysis temperature Tdec of the organic material is 950 (° C.)<(Tdec (° C.)−20)/k<4100° C., and the absorption coefficient "k" is k>0.0;

a carrier (C) /noise (N) ratio of C/N>43 dB; wherein the organic material is a dye or a pigment selected from the group consisting of azo, merocyanines, hemicyanines, strepto cyanines, zero cyanines, enamine, hydrazone, coumarines and phthalocyanines; and wherein recording and reproducing is made with an optical system with a numerical aperture of an objective lens of the optical pickup of 0.80 or more, by employing a blue-light source of wavelength of about 360 nm to about 460 nm.

2. An optical recording medium according to claim 1, wherein the organic material represent at feast one compound of the following formulas:

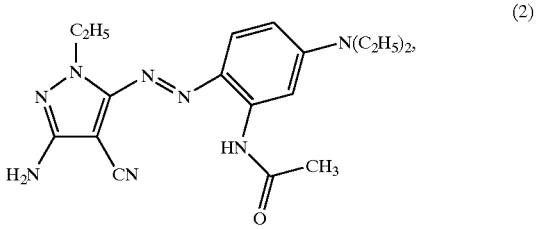
(2)

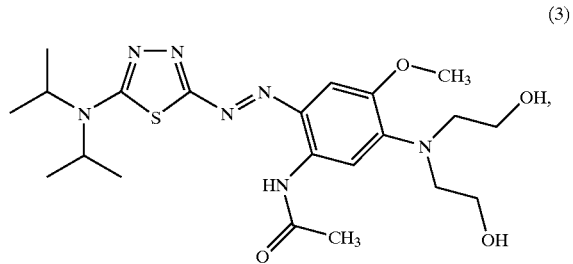
(3)

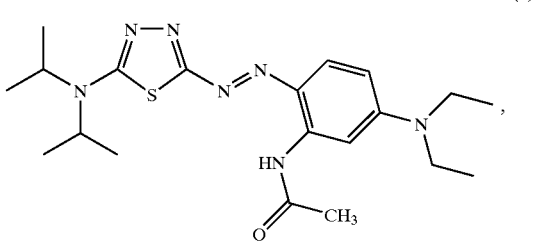
(4)

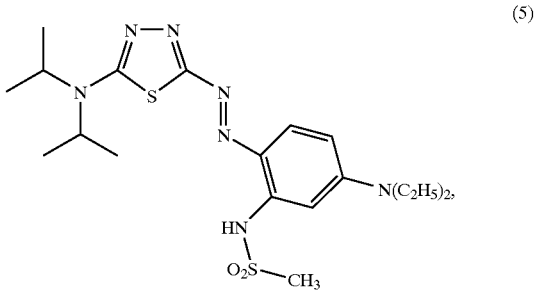
(5)

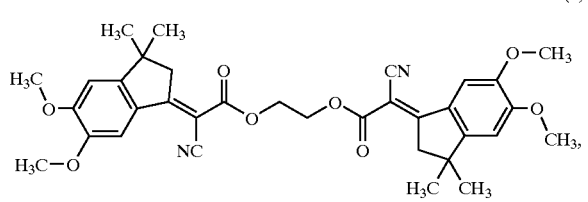
(6)

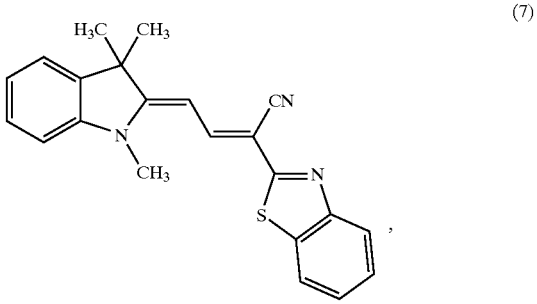
(7)

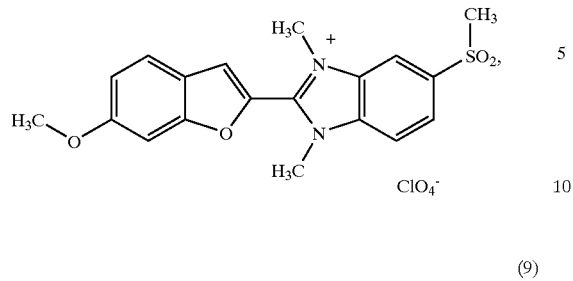
(8)
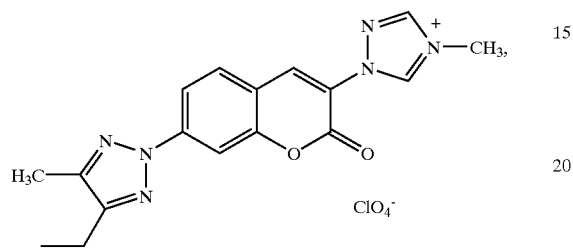
(9)
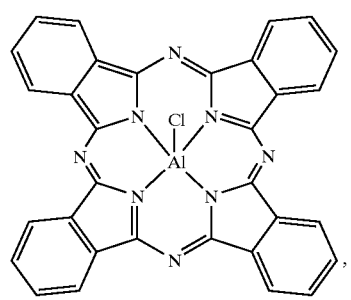
(10)
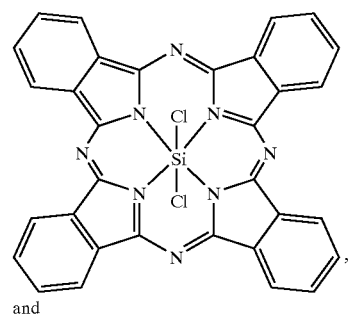
(11)
and
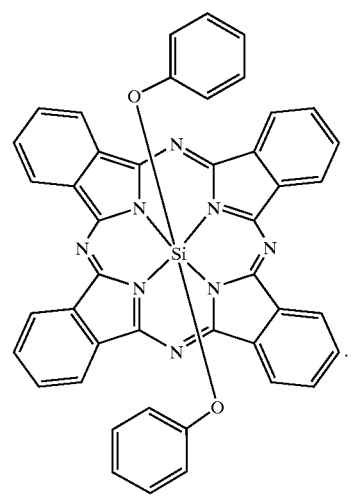
(12)
3. The optical recording of claim 1 wherein the absorption coefficient "k" is k>0.11.
* * * * *